United States Patent [19]

Normandin et al.

[11] Patent Number: 4,942,118
[45] Date of Patent: Jul. 17, 1990

[54] PHOTOGRAPHIC SILVER HALIDE MATERIALS AND PROCESS COMPRISING A PYRAZOLOAZOLE COUPLER

[75] Inventors: Sharon E. Normandin, Macedon; Arlyce T. Bowne, Rochester, both of N.Y.; Nigel E. Milner; David Clarke, both of Watford, Great Britain

[73] Assignee: Eastman Kodak Company, Rochester, N.Y.

[21] Appl. No.: 257,373

[22] Filed: Oct. 13, 1988

Related U.S. Application Data

[63] Continuation of Ser. No. 23,517, Mar. 9, 1987, abandoned.

[51] Int. Cl.$^5$ .............................................. G03C 7/38
[52] U.S. Cl. .................................... 430/558; 430/386; 430/387
[58] Field of Search ..................... 430/386, 387, 558

[56] References Cited

U.S. PATENT DOCUMENTS

| 4,338,393 | 7/1982 | Bailey et al. | 430/387 |
| 4,443,536 | 4/1984 | Lestina | 430/552 |
| 4,540,654 | 9/1985 | Sato et al. | 430/381 |
| 4,600,688 | 7/1986 | Kawakatsu et al. | 430/558 |
| 4,607,002 | 8/1986 | Nakayama et al. | 430/505 |
| 4,639,415 | 1/1987 | Kaneko et al. | 430/558 |
| 4,684,603 | 8/1987 | Nishijima et al. | 430/558 |
| 4,777,121 | 10/1988 | Buckland et al. | 430/386 |

FOREIGN PATENT DOCUMENTS

| 0183444 | 6/1986 | European Pat. Off. . |
| 0183445 | 6/1986 | European Pat. Off. . |
| 60-220346 | 11/1985 | Japan . |
| 1247493 | 9/1971 | United Kingdom . |
| 1252418 | 11/1971 | United Kingdom . |
| 1398979 | 6/1975 | United Kingdom . |

OTHER PUBLICATIONS

Research Disclosure No. 12443, *Research Disclosure*, vol. 124, 1974, Kenneth Mason Publications Ltd., Hampshire, England.
Research Disclosure No. 17643, *Research Disclosure*, vol. 176, 1978, Kenneth Mason Publications Ltd., Hampshire, England.

*Primary Examiner*—Paul R. Michl
*Assistant Examiner*—Mark R. Buscher
*Attorney, Agent, or Firm*—Richard E. Knapp

[57] ABSTRACT

Novel pyrazoloazole couplers comprise an aryl or heterocyclic group having, in at least one of the ortho positions to the carbon atom (A) that is bonded to the pyrazoloazole nucleus, a substituent (B) that enables the pyrazoloazole coupler to form a magenta dye that has increased stability and has absorption controllably shifted, that is shifted hypsochromically relative to a dye formed from a similar coupler lacking substituent (B). These couplers are useful in photogaphic silver halide materials and processes.

8 Claims, No Drawings

PHOTOGRAPHIC SILVER HALIDE MATERIALS AND PROCESS COMPRISING A PYRAZOLOAZOLE COUPLER

This is a continuation of application Ser. No. 023,517, filed Mar. 9, 1987, now abandoned.

This invention relates to novel pyrazoloazole couplers and to photographic silver halide materials and processes using such couplers enabling formation of a magenta dye that has a desired shift in hue and increased stability.

Color images are customarily obtained by reaction between the oxidation product of a silver halide color developing agent and a dye-forming coupler. Pyrazolone dye forming couplers are useful for forming magenta dye images; however, pyrazoloazole couplers represent another class of couplers that are useful for this purpose. Examples of such couplers, such as 1H-pyrazolo[3,2-c]-s-triazole couplers, are described in, for example, U.S. Pat. Nos. 443,536 and 4,540,654; and U.K. Pat. Nos. 1,247,493; 1,252,418 and 1,398,979.

While such magenta dye forming couplers are useful in photographic silver halide materials and processes, many of such couplers provide dyes that do not have the desired properties. Pyrazoloazole couplers, particularly pyrazolotriazole couplers, often form magenta dyes that fall short of desired aims in hue and stability. For example, it has been found that pyrazolotriazole couplers typically form magenta dyes having hues that are shifted hypsochromically relative to the desired hues of dyes formed from pyrazolone couplers. It has also been found that aryl groups on the pyrazoloazole nucleus, for example, an unsubstituted phenyl group in the 3- or 6-position of a 1H-pyrazolo-[3,2-c]-s-triazole, will enable formation of magenta dye having less than desired stability and a hue shifted bathochromically too far for most purposes for conventional photography.

It has also been desirable to provide a pyrazoloazole coupler that forms a magenta dye by reaction of the coupler with an oxidized silver halide color developing agent wherein the magenta dye has increased stability and the photographic sensitivity is not impaired. It has been desirable to provide such dyes that have with increased stability and a narrower absorption half bandwidth (HBW) to improve hue purity and color saturation.

It has been found that a novel dye-forming pyrazoloazole coupler enabling the described advantages has an aryl or heterocyclic group comprising a carbon atom (A) that is bonded to the pyrazoloazole nucleus, wherein the aryl or heterocyclic group comprises a substituent (B) in at least one position ortho to the carbon atom (A), and wherein the substituent (B) enables the dye formed upon reaction of the pyrazoloazole coupler with an oxidized silver halide color developing agent to have increased stability and controllably shifted absorption. The term controllably shifted absorption means that the dye formed from the pyrazoloazole coupler of the invention has an absorption shifted hypsochromically relative to a dye formed from a similar coupler lacking substituent (B).

Such dye-forming couplers are particularly useful in photographic silver halide materials and processes. The substitution in the ortho position of the aryl or heterocyclic group on the pyrazoloazole coupler causes the unexpected shifts in the hue of the dye formed from the pyrazoloazole coupler and enables formation of a dye having increased stability that is particularly useful in such materials and processes.

Pyrazolotriazoles are particularly useful pyrazoloazoles according to the invention. Such pyrazolotriazoles include, for example, a 1H-pyrazolo[2,3-b]-1,2,4-triazole. A 1H-pyrazolo[1,2,4-triazole can also be named as a 1H-pyrazolo[1,5-b]-1,2,4-triazole. The latter nomenclature has been used in the photographic art in, for example, U.S. Pat. No. 4,540,654. The ortho substituted moiety containing carbon atom (A), as described according to the invention, in the case of a pyrazolo[2,3-b]-1,2,4-triazole is in the 2- or 6-position and in the case of a pyrazolo[3,2-c]-s-triazole is in the 6- or 3-position.

It is believed that the steric constraints within the coupler molecule caused by the ortho substituent (B), at least in part, enables the described advantages. For example, it is believed that the 3- or 6-positions of a 1H-pyrazolo[3,2 ]-s-triazole coupler are most sensitive toward hue shifts of the dye formed by changes in substitution. Placement of an electron withdrawing group at the 6-position typically shifts the hue of the dye formed bathochromically. It was surprisingly found that the ortho-substituent on the 6- or 3-position aryl or heterocyclic group caused the dye formed from the coupler to be shifted hypsochromically relative to the dye formed from the unsubstituted coupler by forcing the 6- or 3-substituent, particularly a 6-phenyl substituent, out of the plane of the pyrazolotriazole chromophore by steric constraints. Although the ortho group on the 6- or 3-substituent may in some cases reduce the oxidative coupling reactivity of the coupler, this reduced coupler activity can be increased by other means, such as by making the coupler more hydrophilic, for example by adding at least one water solubilizing group to the coupler. The shift of dye hue formed can be controlled by changing the groups on the 6- or 3-position substituents. The invention accordingly enables tailoring of the dye hue of a dye from a pyrazoloazole coupler to the desired wavelength.

Pyrazoloazole couplers according to the invention have an aryl or heterocyclic group represented by

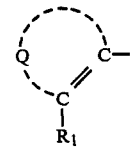

wherein

R₁ is substituent (B), as described, preferably unsubstituted or substituted alkoxy, such as alkoxy containing 1 to 30 carbon atoms, for example, methoxy, ethoxy, propoxy, butoxy, decyloxy and eicosyloxy; halogen, such as chlorine, bromine and fluorine; or alkyl, such as unsubstituted or substituted alkyl containing 1 to 30 carbon atoms, for example, methyl, ethyl, propyl, butyl, pentyl, and eicosyl; and Q represents the atoms necessary to complete an unsubstituted or substituted aryl or heterocyclic group.

$R_1$ can be any substituent that enables the hue of the dye formed from the pyrazoloazole coupler to be controllably shifted, that is shifted hypsochromically to a desired degree relative to the dye formed rom a pyrazoloazole containing no such substituent. For example, $R_1$ is preferably an unsubstituted or substituted alkoxy or alkyl group, or halogen. Unsubstituted or substituted alkoxy and alkyl groups as $R_1$ enable formation of dyes that have unexpectedly improved light stability.

When the described aryl or heterocyclic groups contain two substituents (B) ortho to the carbon atom (A) the dye formed from the pyrazoloazole coupler has improved dye stability compared to a dye formed from a pyrazoloazole coupler containing only one substituent (B) ortho to the carbon atom (A). Highly preferred pyrazoloazole couplers contain a first alkoxy group and a second alkoxy group ortho or para to the first alkoxy group; and, substituent (B) is alkoxy, alkyl or halogen.

The aryl or heterocyclic group completed by Q can be any such group which enables the desired coupling activity of the coupler as well as desired dye hue and stability of the dye formed. Typically useful aryl groups are phenyl or naphthyl groups. Typically useful heterocyclic groups contain 5 or 6 members in the ring and are, for example, pyridyl, furyl, and thienyl groups.

In addition to the substituent (B) as described, the aryl or heterocyclic group containing carbon atom (A) can optionally contain 1 to 4 other groups that do not adversely affect the desired properties of the coupler, for example alkoxy groups, such as alkoxy groups containing 1 to 30 carbon atoms, including methoxy, ethoxy, propoxy, butoxy and alkylenedioxy groups. Other illustrative optional groups on the aryl or heterocyclic group include ethyl, propyl, butyl and pentyl; and, ballast groups known to be useful on photographic couplers.

Illustrative examples of aryl groups containing substituent (B) are as follows:

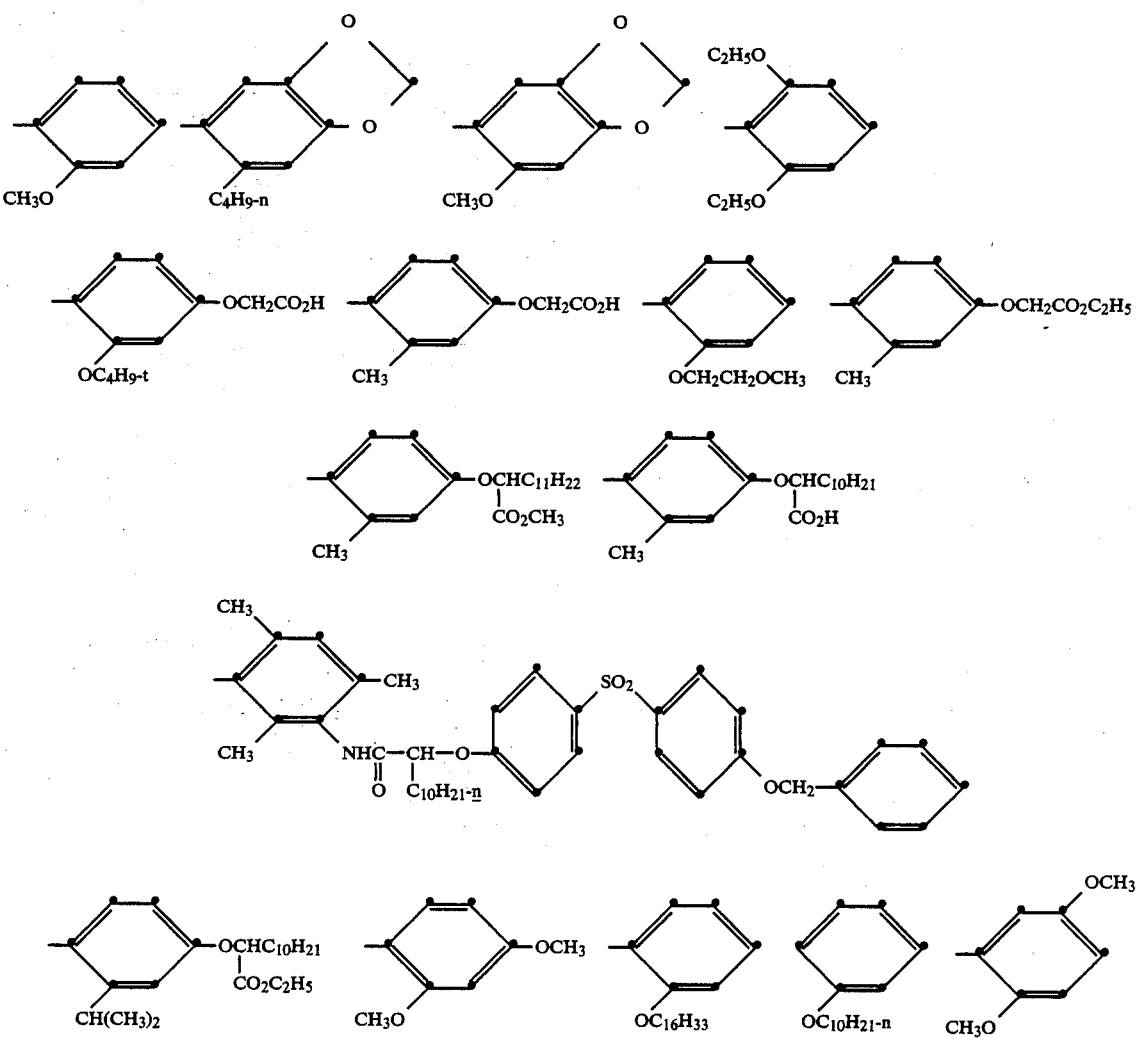

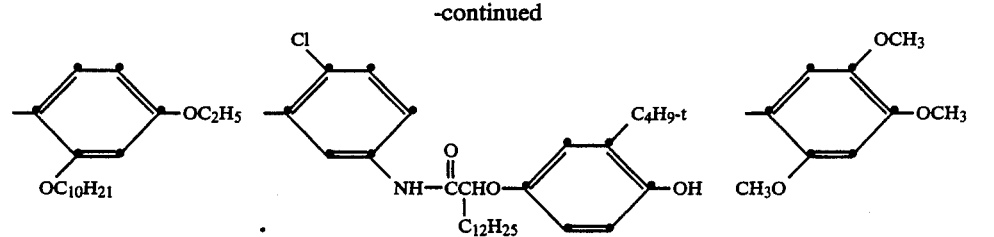
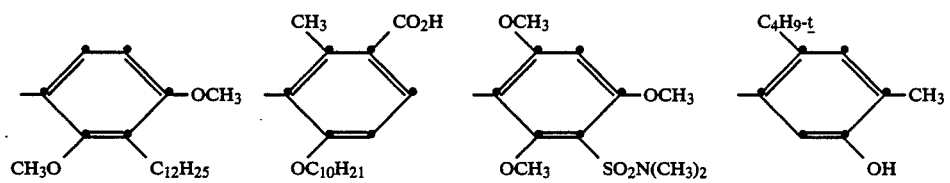
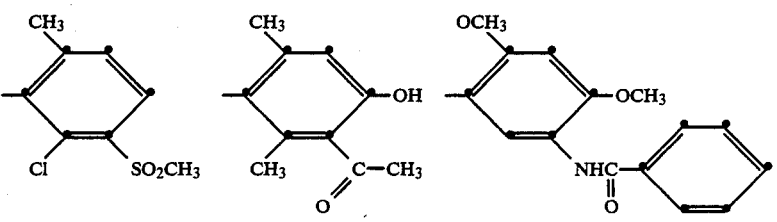
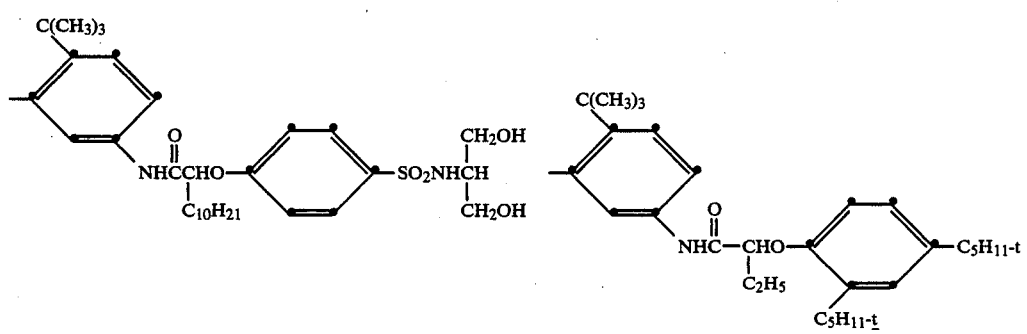
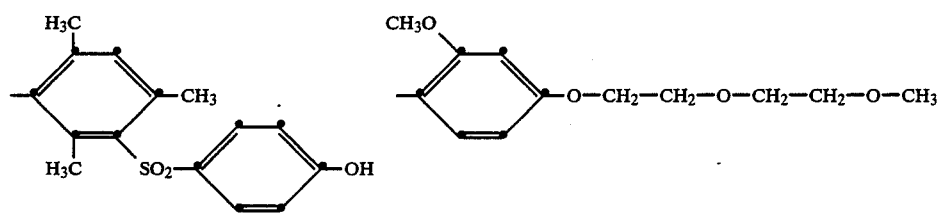
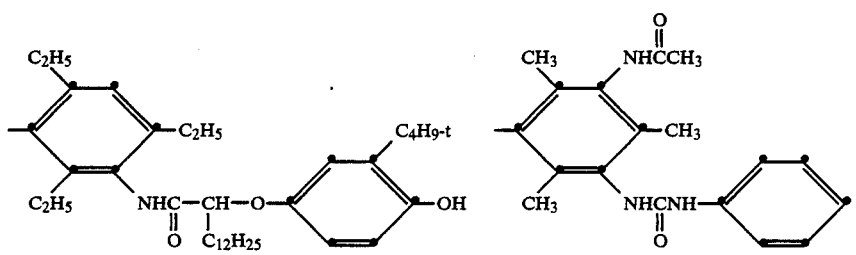
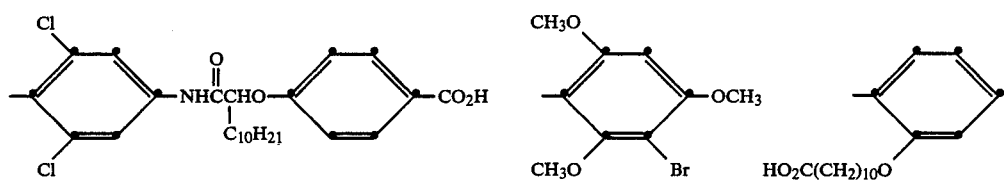

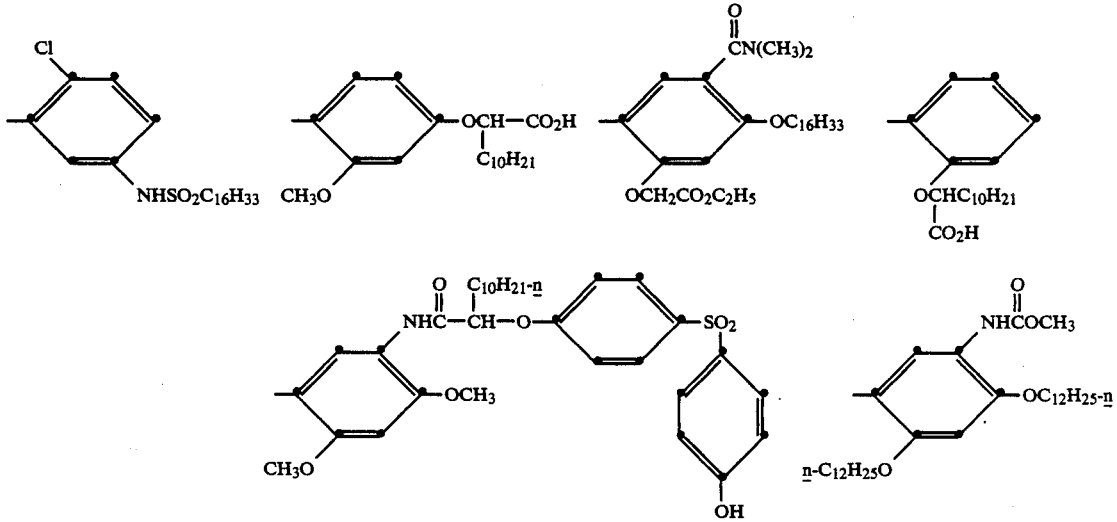

Illustrative examples of heterocyclic groups containing substituent (B) are as follows:

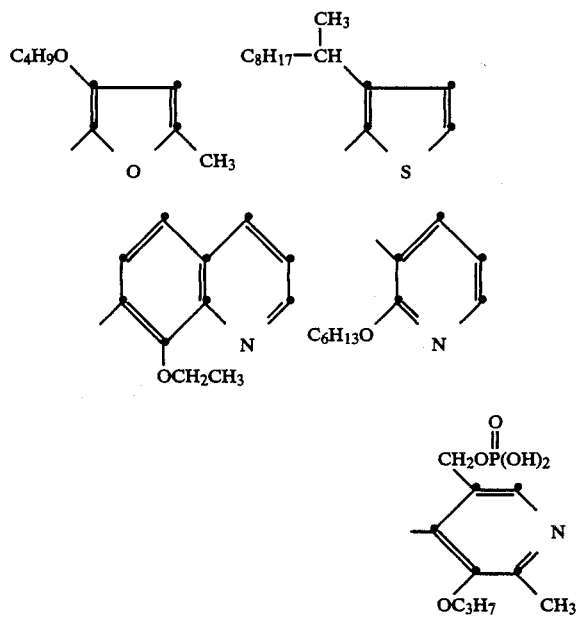

The pyrazoloazole coupler typically contains in a position that does not contain the described aryl or heterocyclic group containing the substituent (B), hydrogen or a group which typically promotes solubility, diffusion resistance or dye hue of the dye formed upon reaction of the coupler with an oxidized color developing agent.

The pyrazoloazole coupler typically contains in a position not containing the described aryl or heterocyclic group containing substituent (B), as described, hydrogen or a group selected from the following:

amino, such as dioctylamino, dimethylamino, and dodecylamino; alkyl, such as alkyl containing 1 to 30 carbon atoms, for example, methyl, ethyl, propyl, n-butyl, t-butyl, octyl and eicosyl; cycloalkyl, such as cyclohexyl and cyclopentyl; aryl, such as aryl containing 6 to 20 carbon atoms, for example, phenyl, naphthyl, and mesityl; carboxy; cyano; nitro; a heterocyclic group, such as a heterocyclic group comprised of atoms selected from carbon, oxygen, nitrogen and sulfur atoms necessary to complete a 5 or 6 member ring, for example, pyrrole, oxazolyl and pyridyl; or $-(L_1)_n-(L_2)_m-R_6$ wherein $L_1$ is a linking group that does not adversely affect the desired properties of the coupler, such as an alkylene, for example, alkylene containing 1 to 20 carbon atoms including methylene, ethylene, propylene, n-butylene, isopropylmethylene, and octylene, or arylene, such as arylene containing 6 to 20 carbon atoms, for example, phenylene and naphthylene; $L_2$ is a linking group that does not adversely affect the desired properties of the coupler, and that is the same as or different from $L_1$, and is typically O, S, CO, $CO_2$, $SO_2$, SO, $$\underset{R_7}{NCO},\ \underset{R_7}{NSO_2},\ \underset{R_7}{CON},\ \underset{R_7}{SO_2N},\ \underset{R_7}{\overset{O}{\overset{\|}{OCN}}},\ \underset{R_7\ R_8}{\overset{}{NCON}}\ \text{and}\ \underset{R_7}{\overset{O}{\overset{\|}{NCO}}}.$$

$R_7$ and $R_8$ are individually hydrogen, alkyl, such as alkyl containing 1 to 20 carbon atoms, for example, methyl, ethyl, propyl, n-butyl, t-butyl, and eicosyl, or aryl, such as aryl containing 6 to 20 carbon atoms, for example, phenyl and naphthyl; n and m are individually 0 or 1; and, $R_6$ is alkyl, such as alkyl containing 1 to 30 carbon atoms, for example, methyl, ethyl, propyl, n-butyl, t-butyl, and octyl, or aryl, such as aryl containing 6 to 20 carbon atoms, for example, phenyl, napthyl, and mesityl; or a heterocyclic group, such as a 5- or 6-member heterocyclic group comprised of atoms selected from carbon, nitrogen, oxygen and sulfur atoms necessary to complete a 5- or 6-member heterocyclic ring, such as an oxazole, pyridine, pyrrole or thiophene ring.

These groups are unsubstituted or optionally substituted with groups that do not adversely affect the desired properties of the pyrazoloazole coupler. Examples of useful substituents can include ballast groups and coupler moieties known to be useful in the photographic art, or alkyl, such as alkyl containing 1 to 4 carbon atoms, for example, methyl, ethyl and t-butyl.

The pyrazoloazole contains in the coupling position, hydrogen or a coupling off group, also known as a leaving group.

Coupling-off groups, defined by Z herein, are well known to those skilled in the art. Such groups can determine the equivalency of the coupler, can modify the reactivity of the coupler, or can advantageously affect the layer in which the coupler is coated or other layers in the element by performing, after release from the coupler, such functions as development inhibition, development acceleration, bleach inhibition, bleach acceleration, color correction, and the like. Representative classes of coupling off groups include halogen, particularly chlorine bromine, or fluorine, alkoxy, aryloxy, hetero- cyclyloxy, sulfonyloxy, acyloxy, carbonamido, imido, acyl, heterocyclylimido, thiocyano, alkylthio, arylthio, heterocyclylthio, sulfonamido, phosphonyloxy and arylazo. They are described in, for example, U.S. Pat. Nos. 2,355,169; 3,227,551; 3,432,521; 3.476,563; 3,617,291; 3,880,661; 4,052.212 and 4,134,766; and in U.K. patents and published application numbers 1,466,728; 1,531,927; 1,533,039; 2,006,755A and 2,017,704A; the disclosures of which are incorporated herein by reference.

Examples of specific coupling off groups are

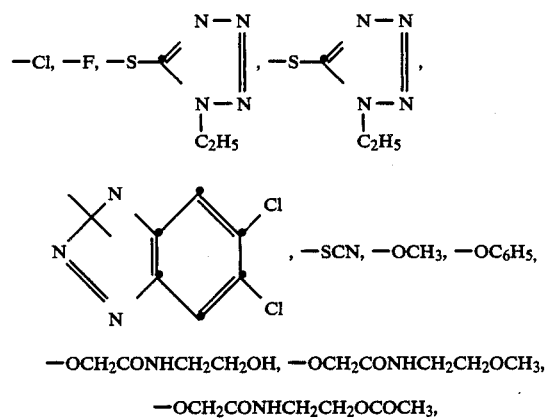

—OCH$_2$CONHCH$_2$CH$_2$OH, —OCH$_2$CONHCH$_2$CH$_2$OCH$_3$,

—OCH$_2$CONHCH$_2$CH$_2$OCOCH$_3$,

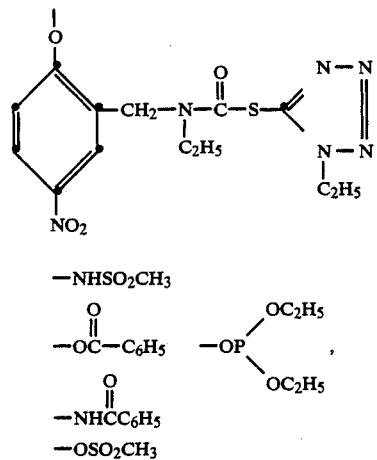

—NHSO$_2$CH$_3$

—OC(=O)—C$_6$H$_5$, —OP(OC$_2$H$_5$)(OC$_2$H$_5$),

—NHCC$_6$H$_5$

—OSO$_2$CH$_3$

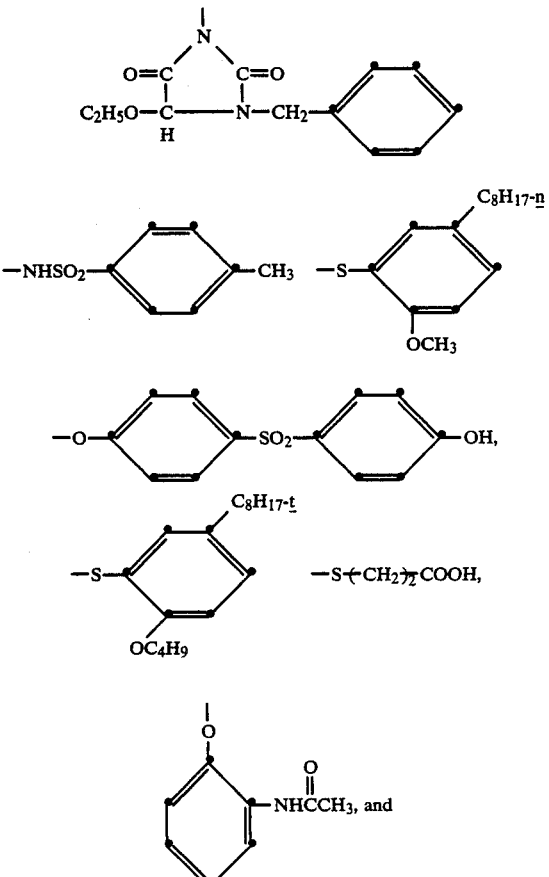

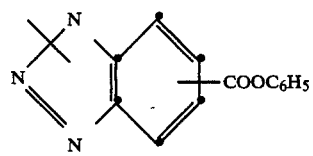

The pyrazoloazoles typically comprise a ballast group. A ballast group as described is an organic radical of such size and configuration as to confer on the coupler molecule sufficient bulk to render the coupler substantially non diffusible from the layer in which it is coated in a photographic element. Couplers of the invention may be attached to ballast groups, or to polymeric chains through one or more of the groups on the pyrazoloazole nucleus. For example, one or more coupler moieties can be attached to the same ballast group. Representative ballast groups include substituted or unsubstituted alkyl or aryl groups containing 8 to 32carbon atoms. Representative substituents include alkyl, aryl, alkoxy, aryloxy, alkylthio, arylthio, hydroxy, halogen, alkoxycarbonyl, aryloxycarbonyl, carboxy, acyl, acyloxy. carbonamido, carbamoyl, alkylsulFonyl, arylsulfonyl, sulfonamido, and sulfamoyl groups wherein the alkyl and aryl substituents and the alkyl and aryl portions of the alkoxy, aryloxy, alkylthio, arylthio, alkoxycarbonyl, arylcarbonyl, acyl, acyloxy, carbonamido, carbamoyl, alkylsulfonyl, arylsulfonyl, sulfonamido, and sulfamoyl substituents containing 1 to 30 carbon atoms and 6 to 30 carbon atoms. respectively, can be further substituted with such substituents.

Particularly useful pyrazoloazole couplers are those that comprise a water solubilizing group for some photographic materials that enables increased reactivity of the coupler. For example, a particularly useful coupler is a pyrazoloazole, as described, comprising a substituent, such as a ballast group, comprising at least one carboxy group.

Illustrative pyrazoloazole couplers are represented by the formula:

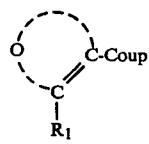

wherein Q and $R_1$ are as described; and, Coup is a pyrazoloazole coupler nucleus, such as a 1H-pyrazolo[3,2-c]-s-triazole or 1H-pyrazolo[2,3-b]-s-triazole nucleus, preferably those pyrazoloazole couplers that enable formation of magenta dyes which have not only a maximum absorption that is controllably shifted but also increased stability.

Preferred 1H-pyrazolo[3,2]-s-triazole couplers are represented by the formula:

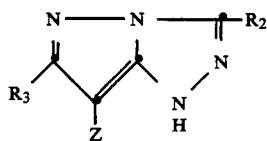

wherein
$R_2$ and $R_3$ are individually hydrogen or a substituent wherein at least one of $R_2$ and $R_3$ is

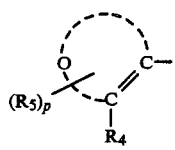

wherein Q represents the atoms necessary to complete an unsubstituted aryl group, such as aryl containing 6 to 30 carbon atoms, for example, phenyl and naphthyl, or heterocyclic group, such as a 5- or 6-member heterocyclic group, for example, pyridyl, furyl and thienyl;

Z is hydrogen or a coupling off group;

$R_4$ is a substituent that enables the maximum absorption of the dye formed upon reaction of the 1H-pyrazolo[3,2-c]-s-triazole coupler with an oxidized silver halide color developing agent to be controllably shifted and enables increased dye stability;

$R_5$ is a substituent group that does not adversely affect the coupler; and p is 0 to 4.

Particularly Preferred couplers are 1H-pyrazolo[3,2-c]-s-triazole couplers represented by the formulas:

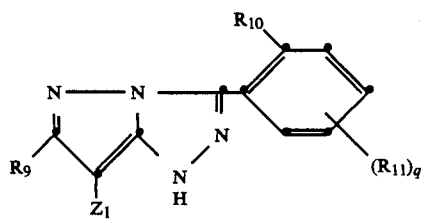

and

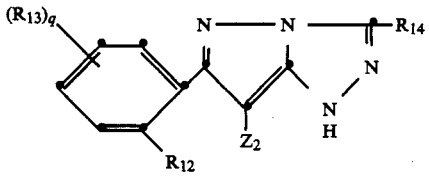

wherein $R_9$ and $R_{14}$ are hydrogen or a substituent that does not adversely affect the coupler, particularly alkyl, such as alkyl containing 1 to 30 carbon atoms, or aryl, such as aryl containing 6 to 20 carbon atoms, or heterocyclic, such as a 5 or 6 member heterocyclic group, for example, pyridyl, furyl and thienyl;

$R_{10}$ and $R_{12}$ are the same as $R_1$, that is substituent (B), as described, preferably unsubstituted alkoxy, such as alkoxy containing 1 to 30 carbon atoms, for example, methoxy, ethoxy, propoxy, butoxy, decyloxy and eicosyloxy; halogen, such as chlorine, bromine and fluorine; or alkyl, such as unsubstituted alkyl containing 1 to 30 carbon atoms, for example, methyl, ethyl, propyl, n-butyl, t-butyl and eicosyl;

$R_{11}$ and $R_{13}$ are the same as $R_5$, as described, that is a substituent that does not adversely affect the coupler;

q is 0 to 4;

$Z_1$ and $Z_2$ are hydrogen or a coupling off group, as described. Especially preferred couplers are those within the above formulas wherein $R_{10}$, $R_{11}$, $R_{12}$ and $R_{13}$ are groups, such as alkoxy groups, that enable the magenta dye formed from the coupler to have increased stability.

Pyrazoloazole couplers, preferably pyrazolotriazole couplers, according to the invention can be used in ways and for purposes that pyrazoloazole couplers have been used in the photographic art.

Pyrazoloazole couplers, particularly, pyrazolotriazole couplers according to the invention are prepared by the general methods of synthesis described in the art, such as in Research Disclosure, August 1974, Item No. 12443 published by Kenneth Mason publications, Ltd., The Old Harbourmaster's, 8 North Street, Emsworth, Hampshire P010 7DD, England and U.S. Pat. No. 4,540,654. An illustrative synthesis scheme I is as follows:

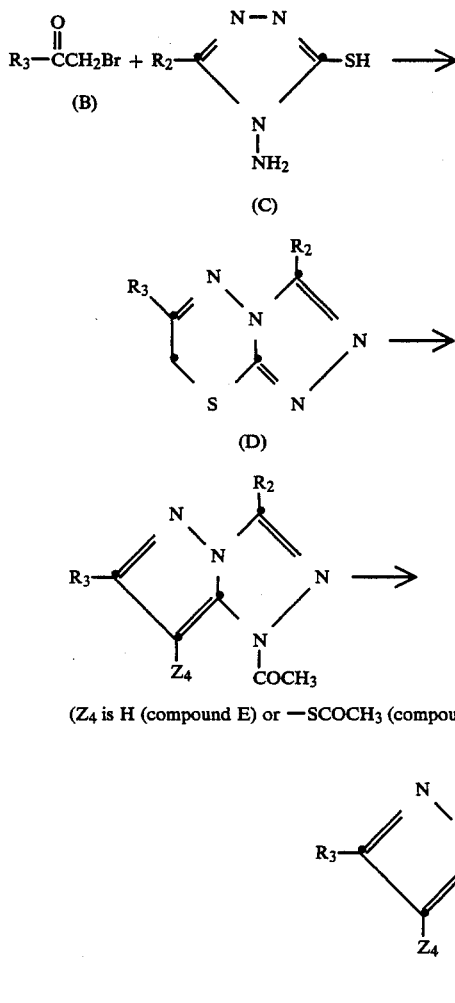

(Z₄ is H (compound E) or —SCOCH₃ (compound E¹))

wherein $R_2$, $R_3$, and $Z_4$ are as described.

In this illustrative synthesis scheme I a methanol or ethanol solution of a bromoketone (B) and a triazole (C) is refluxed 1 to 20 hours to produce triazolothiadiazine (D). The product is neutralized with sodium carbonate. A thermal extrusion of sulfur from the triazolothiadiazine with concurrent ring contraction is carried out by procedures described in *Research Disclosure*, August 1974, Item No. 12443. However, an improvement in the sulfur extrusion from triazolothiadiazine (D) is achieved by refluxing in acetic anhydride to produce compound (E¹) wherein $Z_4$ is SCOCH₃ or by refluxing with triphenylphosphine in acetic anhydride and toluene to produce compound (E) wherein $Z_4$ is H accompanied by a small amount of compound (E¹). Desired pyrazolotriazole (A) wherein Z is H is obtained by treating compound (E) with potassium hydroxide (KOH) or potassium carbonate (K₂CO₃) or by treating compound (E¹) with concentrated hydrochloric acid/glacial acetic acid solution. The coupling-off group, such as chlorine, can be added by procedures known in the organic synthesis art, such as described in, for example, U.K. Patent Specification No. 1,334,515. For example, chlorine can be added as the coupling-off moiety by reaction of the pyrazolotriazole with N-chlorosuc-cinimide in dichloromethane. Particularly useful pyrazolotriazoles that can be prepared by this procedure are pyrazolotriazoles containing a t-butyl group in the 3-position and an aryl group, such as an ortho alkoxy or ortho alkyl substituted phenyl group, in the 6-position, with hydrogen or a coupling-off group in the coupling position.

The intermediate triazole (C) is prepared by methods known in the organic synthesis art. For example, one process is illustrated by the following reactions:

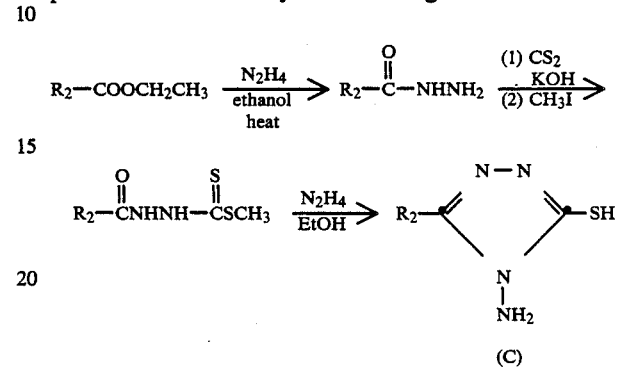

Illustrative examples of synthesis of pyrazoloazole couplers, as described, are as follows: Synthesis Example A - (Synthesis of Compound 6)

A solution of equimolar amounts of bromoketone (B, $R_3$ is 2-methyl-4-α-carbomethoxyundecyloxyphenyl) and triazole (C, $R_2$ is methyl) in methanol was heated to reflux until thin layer chromatography indicated starting materials were consumed. The mixture was concentrated in vacuo, then treated with 10% sodium carbonate solution and extracted with ethyl acetate. The separated organic layer was dried over magnesium sulfate and concentrated to give the desired product (D with $R_2$ and $R_3$ groups described above) as indicated by the following NMR spectrum:

NMR (CDCl₃) δ (ppm): 0.85 (m 3H), 1.1–1.4 (broad s, 16H), 1.9–2.1 (m, 2H), 2.50 (s, 3H), 2.55 (s, 3H), 3.80 (s, 3H), 3.85 (s, 2H), 4.8 (t, 1H), 6.8 (m, 2H), 7.4 (d, 1H).

To a solution of triazolothiadiazine (D) in toluene was added triphenylphosphine (4 molar equivalents), followed by acetic anhydride (2 molar equivalents). The resulting solution was heated to reflux for 2 hrs., cooled and concentrated in vacuo at ~50° C. The residue was immediately vacuum-chromatographed on silica gel G. Pure desulfurized product (E¹ with $R_2$ and $R_3$ groups described above) was isolated in 65% yield and had the following NMR spectrum.

NMR (CDCl₃) δ (ppm): 0.85 (m 3H), 1.1–1.4 (broad s, 16H), 1.9–2.1 (m, 2H), 2.45 (s, 3H), 2.60 (s, 3H), 2.65 (s, 3H), 3.80 (s, 3H), 4.8 (t, 1H), 6.45 (s, 1H), 6.45 (s, 1H), 6.85 (m, 2H), 7.5 (d, 1H).

To a room temperature solution of pyrazolotriazole ester E¹ (4 mmol) in tetrahydrofuran (10 mL) was added 1.1 g (20 mmol) potassium hydroxide in water (10 mL). Sufficient methanol was added to keep the solution homogeneous. After stirring at room temperature for 2 hrs., the reaction mixture was cooled in an ice bath, neutralized with concentrated hydrochloric acid and extracted with methylene chloride. The organic layer was filtered through anhydrous magnesium sulfate and concentrated in vacuo to give an off white solid. Pure product compound 6 (used in Example 6 of Table II) was obtained by trituration with hexane/diethyl ether, as evidenced by its melting point 154°–156° C., NMR, and mass spectra;

NMR (CDCl₃/DMSO -d₆) δ (ppm): 0.85 (m 3H), 1.1–1.4 (broad s, 1H), 1.9–2.1 (m, 2H), 2.45 (s, 3H), 2.55 (s, 3H), 4.8 (t, 1H), 5.8 (s, 1H), 6.7–6.9 (m, 2H), 7.5 (d, 1H). M.S.: M⁺ m/e 426.

Synthesis Example B - (Synthesis of compound 8)

To a solution of pyrazolotriazole compound 6 in methylene chloride (small amounts of CH₃OH may be necessary to achieve complete solution) at room temperature was added 1 molar equivalent N-chlorosuccinimide in several portions. The reaction mixture was then diluted with methylene chloride, washed with water and the organic layer filtered through anhydrous magnesium sulfate and concentrated in vacuo to give compound 8 as a solid product. Pure product having a melting point of 170°–175° C. was obtained by trituration with hexane/diethyl ether and was verified by its NMR and mass spectra:

NMR (DMSO-d6/CDCl₃) δ ppm 0.85 (m, 3H); 1.1–1.4 (broad s 16H); 1.9–2.1 (m, 2H); 2.3 (s, 3 H); 2.55 (s, 3H); 2.6 (s, 1H); 4.65 (t, 1H); 6.7–6.9 (m, 2H); 7.35 (d, 1H). FDMS: m/e 460.

Other 1H -pyrazolo[3,2-c]-s-triazole couplers that can be prepared by procedures similar to those of synthesis Examples A and B are as follows:

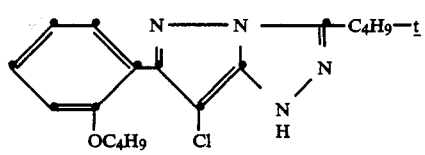

Example C

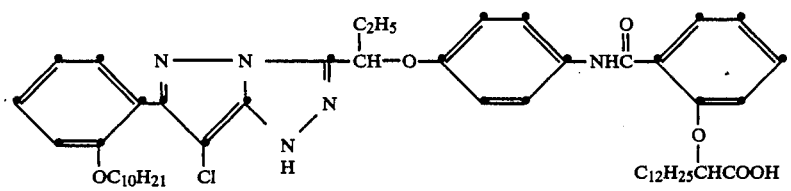

Example D

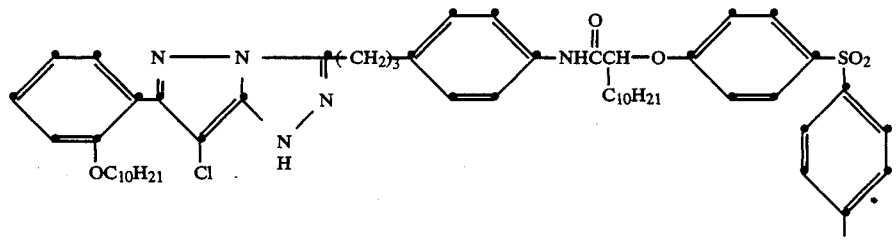

Example E

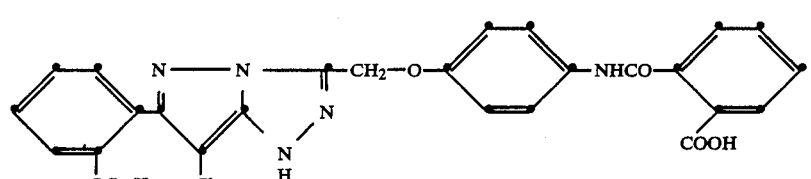

Example F

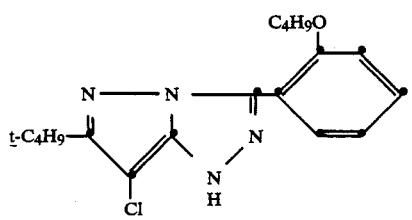

Example G

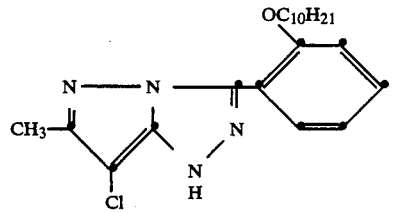

Example H

-continued
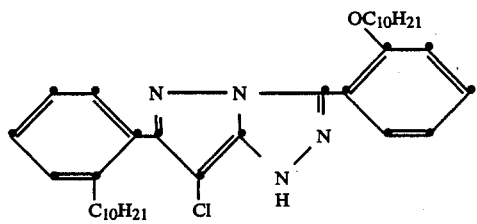
Example I
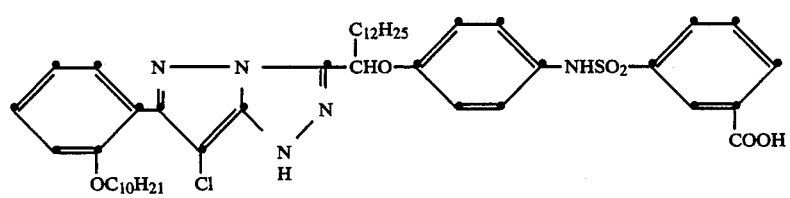
Example J
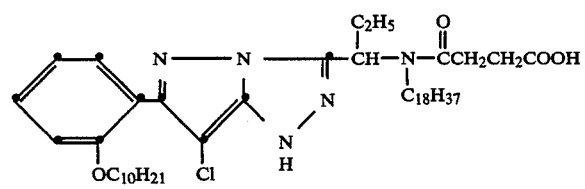
Example K
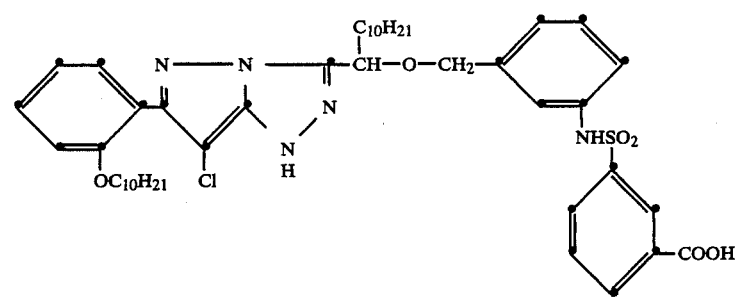
Example L
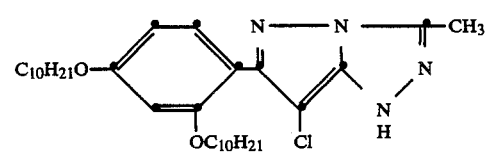
Example M
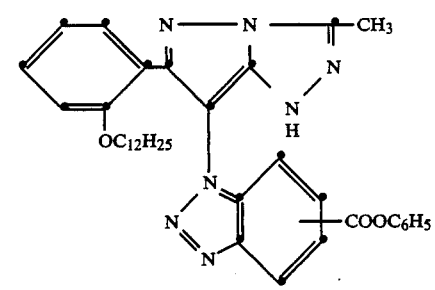
Example N

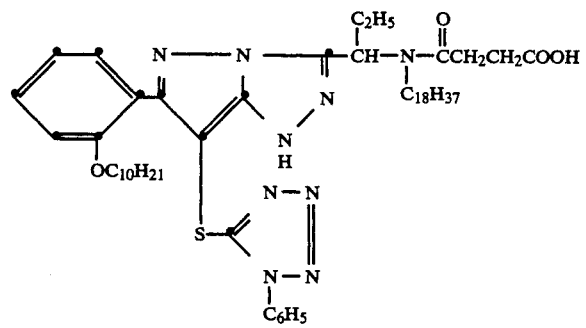
Example O
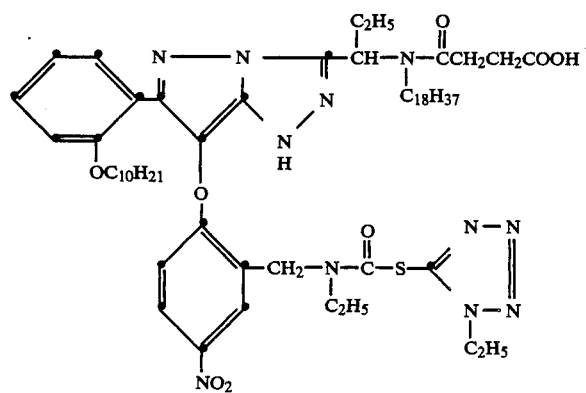
Example P
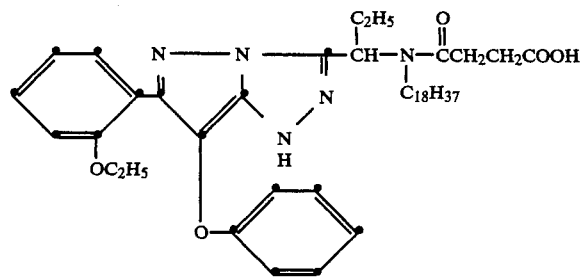
Example Q
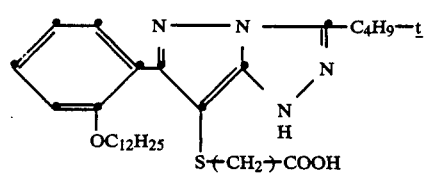
Example R
Other illustrative pyrazoloazole couplers that can be prepared by general procedures described in the art, such as in U.S. Pat. No. 540,654, are as follows:

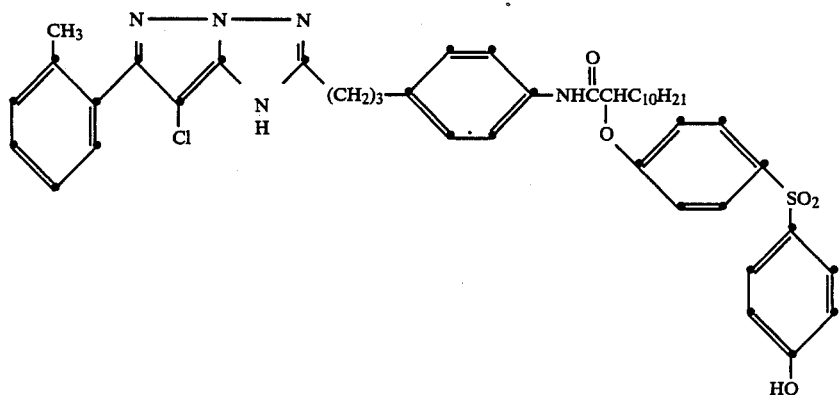
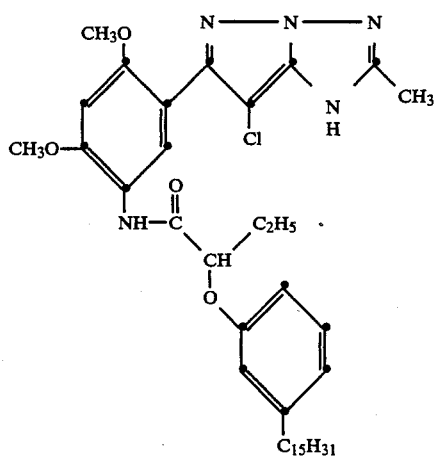
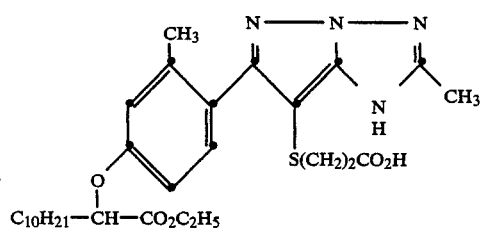
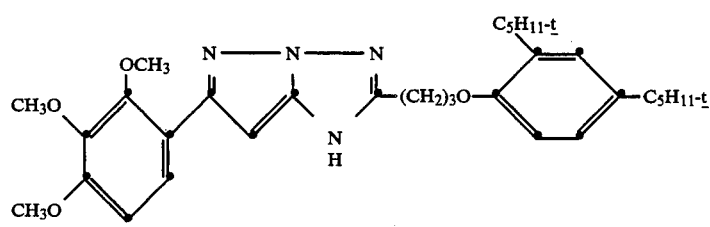
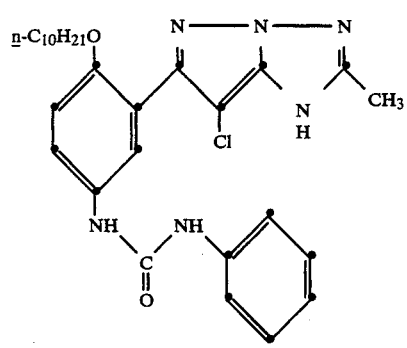

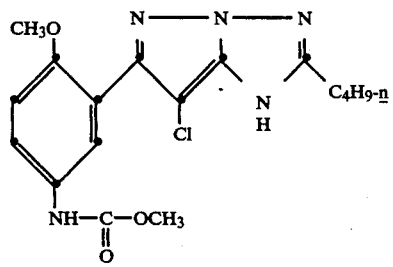
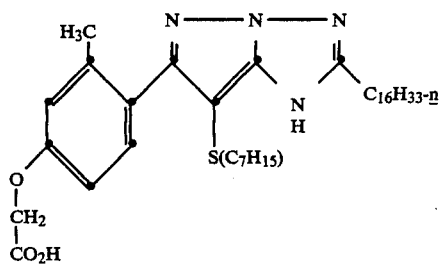
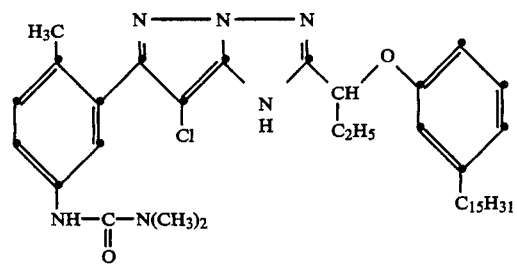
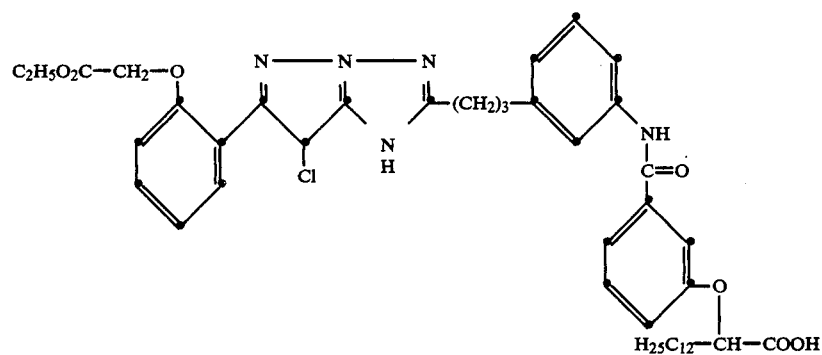
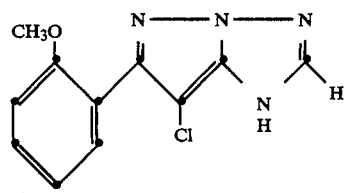
Particularly useful illustrative couplers are pyrazolo[3,2-c]-s-triazoles as follows:

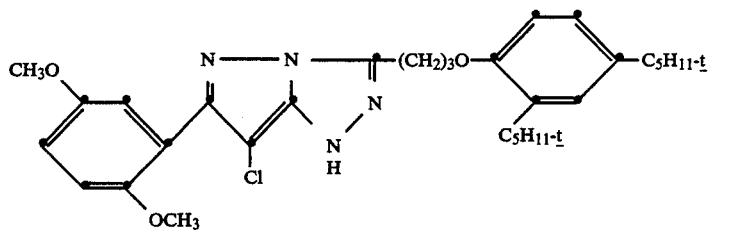
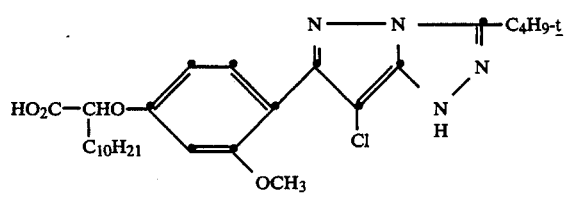
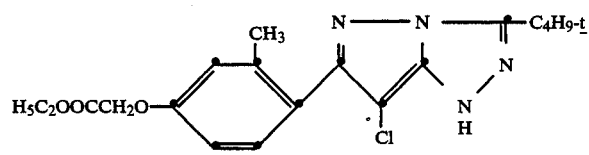
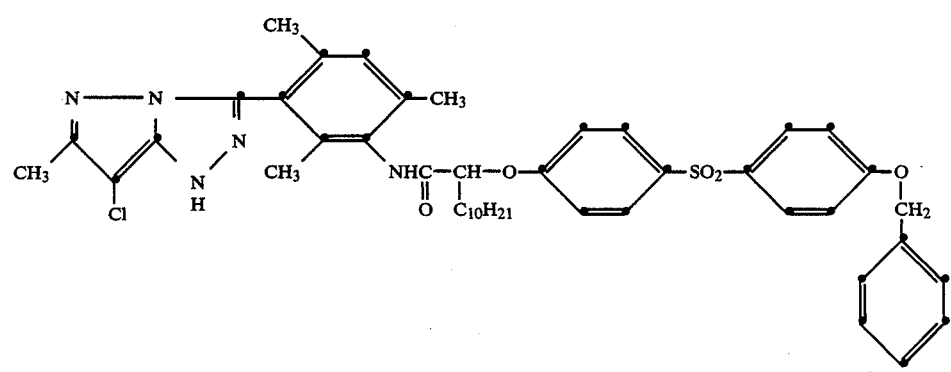
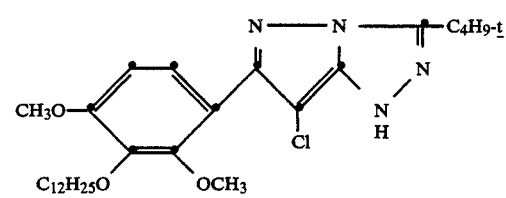
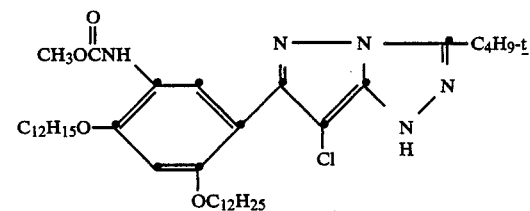
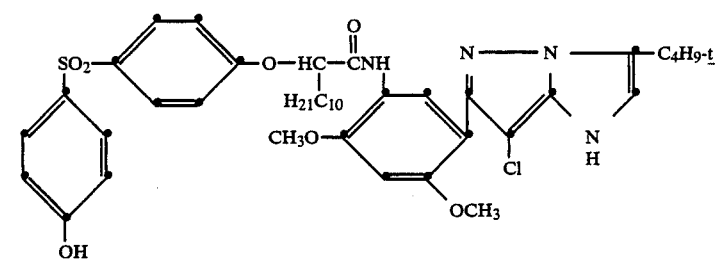

The photographic elements can be single color elements or multicolor elements. In a multicolor element, The dye forming coupler of this invention is typically associated with a green-sensitized emulsion, although it could be associated with an unsensitized emulsion or an emulsion sensitized to a different region of the spectrum. Multicolor elements typically contain dye image forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsion sensitive to each of the three primary regions of the spectrum can be disposed as a single segmented layer.

A typical multicolor photographic element comprises a support bearing a cyan dye image forming unit comprised of at least one red sensitive silver halide emulsion layer having associated therewith at least one cyan dye forming coupler, a magenta dye image-forming unit comprising at least one green-sensitive silver halide emulsion layer having associated therewith at least one magenta dye forming coupler of this invention and a yellow dye image-forming unit comprising at least one blue sensitive silver halide emulsion layer having associated therewith at least one yellow dye forming coupler. The element can contain additional layers, such as filter layers, interlayers, overcoat layers, subbing layers, and the like.

In the following discussion of examples of materials useful in the emulsions and elements of this invention, reference will be made to *Research Disclosure*. December 1978, Item No. 17643, the disclosures of which are incorporated herein by reference. This publication will be identified hereafter by the term "*Research Disclosure*".

The silver halide emulsions employed in the elements of this invention can be either negative working or positive working. Examples of useful emulsions and their preparation are described in *Research Disclosure* Sections I and II and the publications cited therein. Examples of useful vehicles for the emulsion layers of elements of this invention are described in *Research Disclosure* Section IX and the publications cited therein.

In addition to the couplers of this invention, the elements of the invention can include additional couplers, such as described in *Research Disclosure* Section VII, paragraphs D, E, F and G and the publications cited therein. These couplers can be incorporated in the elements and emulsion as described in *Research Disclosures* of Section VII, Paragraph C and the publications cited therein.

The photographic elements of this invention or individual layers thereof, can contain brighteners (see *Research Disclosure* Section V), antifoggants and stabilizers (See *Research Disclosure* Section VI), antistain agents and image dye stabilizer (see *Research Disclosure* Section VII, paragraphs I and J), light absorbing and scattering materials (see *Research Disclosure* Section VIII), hardeners (see *Research Disclosure* Section XI), plasticizers and lubricants (see *Research Disclosure* Section XIII), matting agents (see *Research Disclosure* Section XVI) bleach accelerator and development modifiers (see *Research Disclosure* Section XXI) colored masking couplers, and competing couplers.

The photographic elements can be coated on a variety of supports as described in Research Disclosure Section XVII and the references described therein.

Photographic elements can be exposed to actinic radiation, typically in the visible region of the spectrum, to form a latent image as described in *Research Disclosure* Section XVIII and then processed to form a visible dye image as described in *Research Disclosure* Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-3 -methyl-N,N-diethylaniline hydrochloride,
4-amino-3 -methyl-N-ethyl-N-$\beta$-methanesulfonamido)ethylaniline sulfate hydrate,
4-amino-3-methyl-N-ethyl-N-$\beta$-hydroxyethylaniline sulfate,
4 amino-3-$\beta$-(methanesulonamido)ethyl-N,N-diethylaniline hydrochloride and
4 amino-N-ethyl N-(2)-methoxyethyl)-m-toluidine-di-p-toluenesulfonic acid.

With negative working silver halide this processing step leads to a negative image. To obtain a positive (or reversal) image, this step can be preceded by development with a non-chromogenic developing agent to develop exposed silver halide, but not form dye, and then uniform forging of the element to render unexposed silver halide developable. Alternatively, a direct positive emulsion can be employed to obtain a positive image.

Development is followed by the conventional steps of bleaching, fixing, or bleach fixing, to remove silver and silver halide, washing and drying.

The following examples further illustrate the invention.

EXAMPLES 1-15

Photographic elements were prepared by coating a cellulose acetate butyrate film support with a photosensitive layer containing a silver bromoiodide emulsion at 0.91 g Ag/m$^2$, gelatin at 3.78 g/m$^2$, and one of the couplers identified in Table I or Table II dispersed in one half its weight of tricresyl phosphate and coated at 1.62 mmoles/m$^2$. The photosensitive layer was overcoated with a layer containing gelatin at 1.08 g/m$^2$ and bisvinyl sulfonylmethyl ether at 1.75 weight percent based on total gelatin.

Samples of each element were imagewise exposed through a graduated-density test object and processed at 40° C. employing one of three color developing solutions identified below then stopped, bleached, fixed and washed.

| | Developer Formulations: | | |
|---|---|---|---|
| | D-1 | D-2 | D-3 |
| 4-Amino-3-methyl N,N-diethylaniline hydrochloride | 2.45 g | — | — |
| 4-Amino-3-methyl-N-ethyl-N-β-(methanesulfonamido)ethylaniline sulfate | — | 5.0 g | — |
| 4-Amino-3-methyl-N-ethyl-N-β-hydroxyethyl aniline sulfate | — | — | 3.55 g |
| Potassium sulfite | 2.0 g | 2.0 g | 2.0 g |
| Potassium carbonate (anhydrous) | 30.0 g | 30.0 g | 30.0 g |
| Potassium bromide | 1.25 g | 1.25 g | 1.25 g |
| Potassium iodide | 0.6 mg | 0.6 mg | 0.6 mg |
| 1% Solution in methanol of 5-nitro-1H-indazole | 4.0 mL | — | — |
| Water to: | 1.0 L | 1.0 L | 1.0 L |
| pH adjusted to: | 10.0 | 10.0 | 10.0 |

The well defined magenta dye images produced in each element were evaluated by several tests and measurements. Dye hues were evaluated from spectrophotometric curves by measuring the maximum absorption peak (Lmax) normalized to a density of 1.0. The half bandwidth (HBW), an indication of hue purity, was measured as the width, in nanometers, of the spectrophotometric curve at one-half the difference between the maximum density and stain. Accelerated keeping tests on the dye image of initial density close to 1.0 gave the reported magenta density changes under the following conditions:

LF-3 - 3 week light fading under 5.4 Klux xenon simulated average north skylight.

WO-2 - 2 week "wet oven" dark keeping, 60° C./70% R.H.

DO-1 - 1 week "dry oven" dark keeping, 77° C./5% R.H.

Comparison Coupler A:

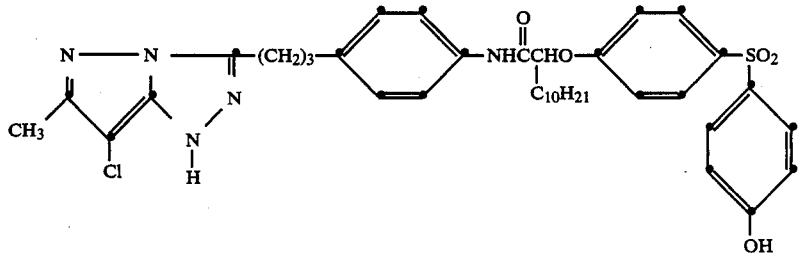

TABLE I

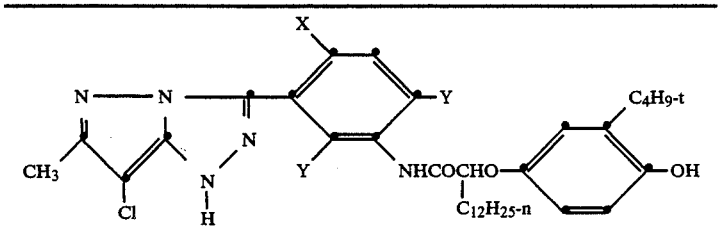

| Coupler | X | Y | LF-3 | WO-2 | DO-1 | Lmax | HBW |
|---|---|---|---|---|---|---|---|
| Compr. A | (See structure) | | −.56 | +.06 | n/a | 556 | 82 |
| Compr. B | H | H | −1.01 | +.07 | +.03 | 546sh, 573 | 113 |
| Exmpl. 1 | Cl | H | −.62 | +.06 | +0.1 | 569 | 92 |
| Exmpl. 2 | CH$_3$ | H | −.62 | +.05 | +.03 | 555 | 107 |
| Exmpl. 3 | CH$_3$ | CH$_3$ | −.30 | +.02 | +.01 | 557 | 81 |
| Exmpl. 4 | C$_2$H$_5$ | C$_2$H$_5$ | −.15 | +.05 | +.02 | 557 | 77 |
| Exmpl. 5 | C$_3$H$_7$-i | C$_3$H$_7$-i | *n/a | *n/a | *n/a | 557 | 75 |

Developer D-1 was used to obtain Table I data. Absorption peak shoulder is indicated by "sh".
*n/a means not available.

It can be seen from the data in Table I that an ortho substituent on an aryl ring attached to the 3 position of the pyrazoloazole coupler nucleus provides improved resistance to light fade and comparable or better resistance to fade under heat and humidity when compared to Comparison Coupler B which has no ortho substituent. In addition, a purer hue (narrower HBW) is also attained. Marked improvements in light fade and slightly more bathochromic and purer hues than provided by previously known Comparison Coupler A are achieved when two ortho substituents are present as in

EXAMPLES 3-5.

Direct comparisons for a number of coupler structures bearing a 6 position aryl group are made in Table II between Comparison Couplers C, D, E, F, G, H having no ortho substituent and inventive coupler Examples 6, 7, 8, 9, 10, 11, respectively, which have alkyl or alkoxy ortho substituents. It can be seen that in each case such ortho substitution results in improved resistance to light fade. Examples 13 and 15 show an even more remarkable improvement in light fade resistance when two alkoxy substituents are para to each other rather than meta to each other as in Examples 12 and 14, respectively. Dye hue improvements also generally result from ortho substitution according to the invention, allowing one to control the degree of bathochromic shift from the hue position of known Comparison Coupler A while maintaining a narrow half-bandwidth.

can be effected within the spirit and scope of the invention.

What is claimed is:

1. In a photographic element comprising a support, a photographic silver halide emulsion and a dye-forming pyrazoloazole coupler having an aryl or heterocyclic group comprising a carbon atom (A) that is bonded directly to the pyrazoloazole nucleus, the improvement wherein the aryl or heterocyclic group comprises a

TABLE II

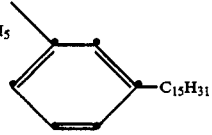

| Coupler | $Z_5$ | $R_{15}$ | X | (Y)n | LF-3 | Lmax | HBW |
|---|---|---|---|---|---|---|---|
| Compr. A | | | | (See structure) | −67 | 554 | 88 |
| Compr. C | H | $CH_3$ | H | 4′-Bal-1a | −83 | 535, 575sh | 126 |
| Exmpl. 6 | H | $CH_3$ | $CH_3$ | 4′-Bal-1a | −36 | 563 | 102 |
| Compr. D | Cl | $C_4H_9$-t | H | 4′-Bal-1a | −6 | 575 | 125 |
| Exmpl. 7 | Cl | $C_4H_9$-t | $CH_3$ | 4′-Bal-1a | −52 | 559 | 85 |
| Compr. E | Cl | $CH_3$ | H | 4′-Bal-1a | −71* | 563 | 102 |
| Exmpl. 8 | Cl | $CH_3$ | $CH_3$ | 4′-Bal-1a | −43* | 559 | 93 |
| Compr. F | Cl | $CH_3$ | H | 4′-Bal-1b | −66 | 566 | 99 |
| Exmpl. 9 | Cl | $CH_3$ | $CH_3$ | 4′-Bal-1c | −44 | 562 | 79 |
| Compr. G | Cl | Bal-2 | H | 4′-$OCH_2COOC_2H_5$ | −48 | 572 | 85 |
| Exmpl. 10 | Cl | Bal-2 | $CH_3$ | 4′-$OCH_2COOC_2H_5$ | −45 | 569 | 74 |
| Compr. H | Cl | $CH_3$ | H | 5′-Bal-3 | −82* | 577 | 89 |
| Exmpl. 11 | Cl | $CH_3$ | $OCH_3$ | 4′-$OCH_3$, 5′-Bal-3 | −23* | 567 | 93 |
| Exmpl. 12 | H | Bal-4 | $OCH_3$ | 4′-$OCH_3$ | −15 | 561 | 78 |
| Exmpl. 13 | H | Bal-4 | $OCH_3$ | 5′-$OCH_3$ | −5 | 565 | 77 |
| Exmpl. 14 | Cl | Bal-4 | $OCH_3$ | 4′-$OCH_3$ | −30 | 557 | 76 |
| Exmpl. 15 | Cl | Bal-4 | $OCH_3$ | 5′-$OCH_3$ | −9 | 563 | 76 |

*Data using developer D-2; all other data using developer D-3. (Absorption peak shoulder is indicated by "sh".)
Bal-1a is —$OCH(C_{10}H_{21})COOH$
Bal-1b is —$OCH(C_{10}H_{21})COOC_2H_5$
Bal-1c is —$OCH(C_{10}H_{21})COOCH_3$ Bal-2 is

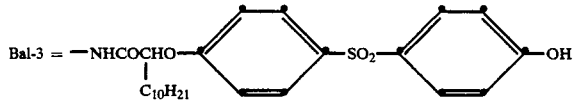

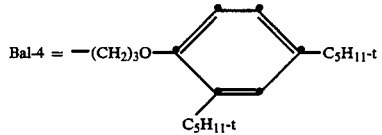

The invention has been described in detail with particular reference to preferred embodiments thereof, but it will be understood that variations and modifications substituent (B) that is a first alkoxy group in at least one position ortho to the carbon atom (A) and the aryl or heterocyclic group, comprises a second alkoxy group, wherein the substituents (B) enables the maximum absorption of dye formed upon reaction of the pyrazoloazole coupler with an oxidized silver halide color developing agent to be controllably shifted and enables increased dye stability.

2. A photographic element as in claim 1 wherein the pyrazoloazole coupler is a 1-H-pyrazolo[3,2-c]-s-triazole is substituted in the 3- or 6-position with an aryl or heterocyclic group containing the substituent (B).

3. A photographic element as in claim 1 wherein the pyrazoloazole coupler is a 1H-pyrazolo[2,3-b]-s-triazole that is substituted in the 2- or 6-position with an aryl or heterocyclic group containing the substituent (B).

4. A photographic element as in claim 1 wherein the pyrazoloazole coupler is a 1H-pyrazolo[3,2-c]-s-triazole coupler that contains in the 3- or 6-position an ortho-substituted phenyl group selected from the following:

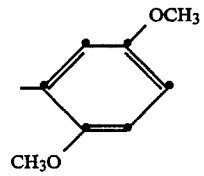

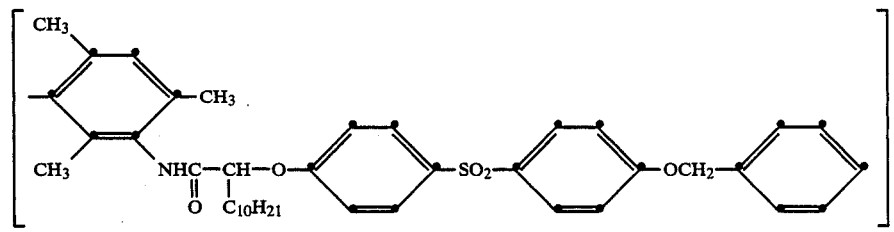

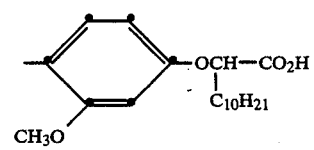

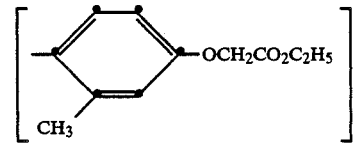

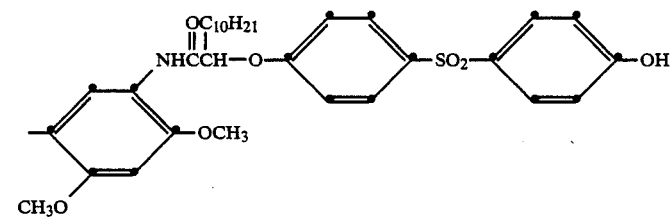

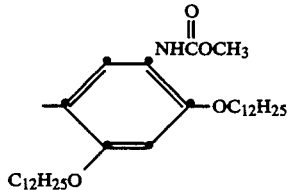

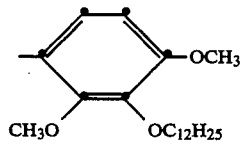

5. A photographic element as in claim 1 comprising a red-sensitive silver halide emulsion unit having associated therewith a cyan dye image providing material, a green-sensitive silver halide emulsion unit having associated therewith a magenta dye image-providing material, and a blue-sensitive silver halide emulsion unit having associated therewith a yellow dye image-providing silver halide material wherein the pyrazoloazole coupler is in at least one of said units.

6. A photographic element as in claim 1 wherein the pyrazoloazole coupler is a compound selected from the group consisting of

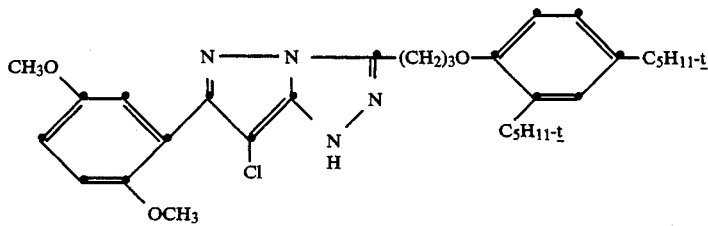

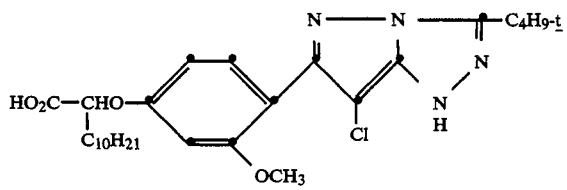

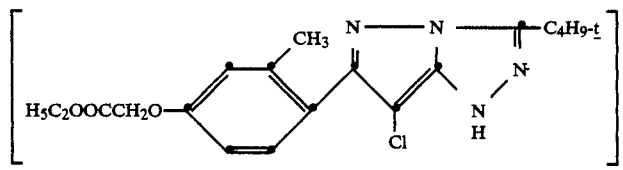

-continued
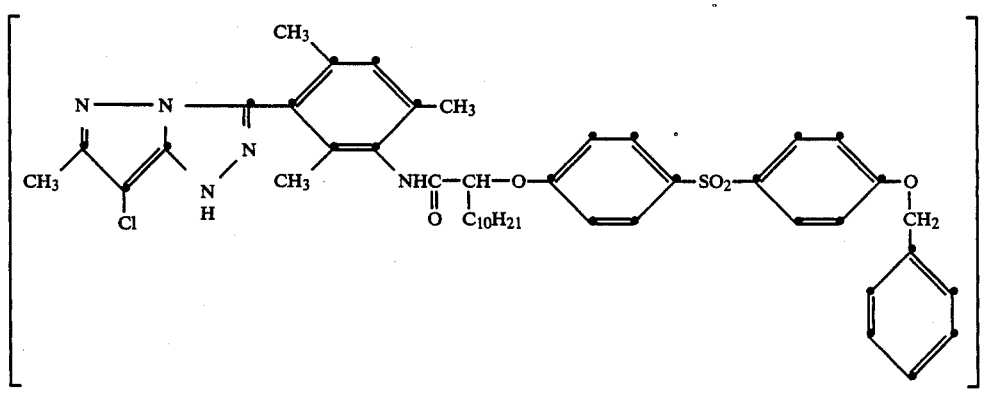
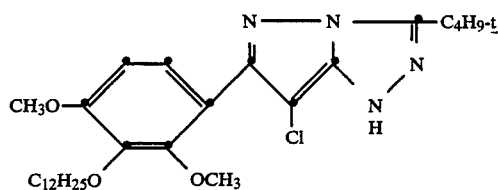
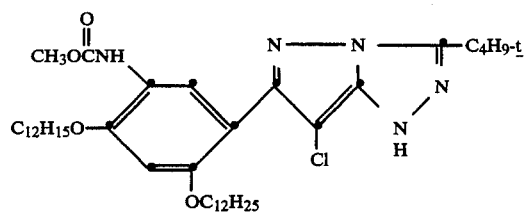
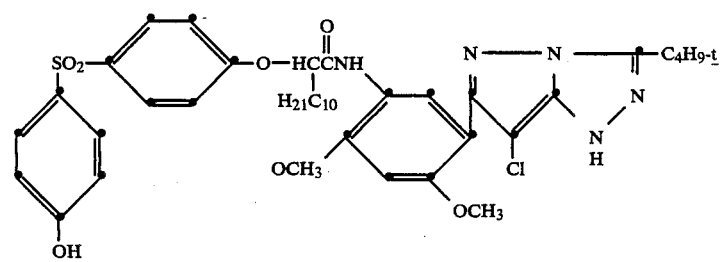
7. A process of forming a magenta dye image in an exposed photographic element as defined in claim 1, said process comprising developing the exposed photographic element with a silver halide color developing agent.
8. A process as in claim 7 wherein the silver halide color developing agent is a p-phenylenediamine.
* * * * *

UNITED STATES PATENT AND TRADEMARK OFFICE
CERTIFICATE OF CORRECTION

PATENT NO. : 4,942,118
DATED : July 17, 1990
INVENTOR(S) : Normandin et al

It is certified that error appears in the above-identified patent and that said Letters Patent are hereby corrected as shown below:

Title page, 2nd column, third line from bottom, "photogaphic" should read --photographic--.

Column 1, line 22, "443,536" should read --4,443,536--.

Column 2, line 13, "1H-pyrazolo[1,2,4-triazole" should read -- 1H-pyrazolo[2,3-b]-1,2,4-triazole --; line 27, "1H-pyrazolo[3,2]-s-triazole" should read -- 1H-pyrazolo[3,2-c]-s-triazole --.

Column 3, line 9, "rom" should read --from--.

Column 10, line 62, "alkylsulFongl" should read --alkylsulfonyl--.

Column 11, lines 15-20,

   should read   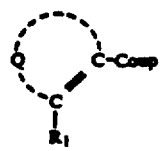

Column 11, line 30, "1H-pyrazolo[3,2]-s-triazole" should read -- 1H-pyrazolo[3,2-c]-s-triazole --.

UNITED STATES PATENT AND TRADEMARK OFFICE
CERTIFICATE OF CORRECTION

Page 2 of 3

PATENT NO. : 4,942,118
DATED : July 17, 1990
INVENTOR(S) : Normandin et al

It is certified that error appears in the above-identified patent and that said Letters Patent are hereby corrected as shown below:

Column 11, lines 44-49,

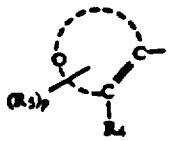   should read   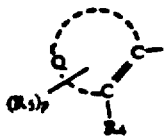

Column 11, line 66, "Preferred" should read --preferred--.

Column 28, line 30, that part of formula reading "4 amino-3-β-(methanesulonamido) )" should read -- 4-amino-3-β-(methanesulfonamido) ) --; line 32, that part of formula reading "4 amino" should read -- 4-amino --; line 40, "forging" should read --fogging--.

Column 30, Table I, under heading DO-1, "+0.1" should read --+.01--.

Column 33, line 3, "group, comprises" should read --group comprises --; line 4, "substituents" should read --substituent--.

Columns 33-34, second formula (in brackets) should have been omitted;

UNITED STATES PATENT AND TRADEMARK OFFICE
CERTIFICATE OF CORRECTION

PATENT NO. : 4,942,118
DATED : July 17, 1990
INVENTOR(S) : Normandin et al

It is certified that error appears in the above-identified patent and that said Letters Patent are hereby corrected as shown below:

Columns 33-34, fourth formula (in brackets) should have been omitted.

Columns 35-36, last formula (in brackets) should have been omitted.

Columns 37-38, first formula (in brackets) should have been omitted.

Signed and Sealed this

Twelfth Day of May, 1992

Attest:

DOUGLAS B. COMER

Attesting Officer

Acting Commissioner of Patents and Trademarks